(12) United States Patent
Reschke

(10) Patent No.: US 8,968,358 B2
(45) Date of Patent: Mar. 3, 2015

(54) BLUNT TISSUE DISSECTION SURGICAL INSTRUMENT JAW DESIGNS

(75) Inventor: Arlan J. Reschke, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1077 days.

(21) Appl. No.: 12/535,869

(22) Filed: Aug. 5, 2009

(65) Prior Publication Data

US 2011/0034918 A1    Feb. 10, 2011

(51) Int. Cl.
| | |
|---|---|
| *A61B 17/28* | (2006.01) |
| *A61B 18/14* | (2006.01) |
| *A61B 17/295* | (2006.01) |
| *A61B 17/32* | (2006.01) |
| *A61B 17/00* | (2006.01) |
| *A61B 17/29* | (2006.01) |
| *A61B 17/3211* | (2006.01) |

(52) U.S. Cl.
CPC .......... *A61B 17/2812* (2013.01); *A61B 17/282* (2013.01); *A61B 17/295* (2013.01); *A61B 18/1442* (2013.01); *A61B 17/32* (2013.01); *A61B 18/1445* (2013.01); *A61B 2017/00353* (2013.01); *A61B 2017/2936* (2013.01); *A61B 2017/2945* (2013.01); *A61B 2017/320052* (2013.01); *A61B 2017/320064* (2013.01); *A61B 2017/32113* (2013.01); *A61B 2018/1432* (2013.01); *A61B 2017/320044* (2013.01)
USPC ................ 606/207; 600/205; 606/51; 606/52

(58) Field of Classification Search
USPC ...................... 606/51–52, 205–211
See application file for complete search history.

(56) References Cited

U.S. PATENT DOCUMENTS

| | | | |
|---|---|---|---|
| 3,862,630 A | | 1/1975 | Balamuth |
| 4,732,149 A | * | 3/1988 | Sutter ............................. 606/51 |
| 4,976,718 A | * | 12/1990 | Daniell ......................... 606/131 |
| 5,460,629 A | | 10/1995 | Shlain et al. |
| 5,549,627 A | * | 8/1996 | Kieturakis .................... 606/206 |
| 5,591,181 A | | 1/1997 | Stone et al. |
| 5,599,279 A | * | 2/1997 | Slotman et al. ............... 600/201 |
| 5,665,100 A | | 9/1997 | Yoon |
| 5,674,220 A | | 10/1997 | Fox et al. |
| 5,755,717 A | | 5/1998 | Yates et al. |
| 5,797,927 A | | 8/1998 | Yoon |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 12/176,679, filed Jul. 21, 2008.

(Continued)

*Primary Examiner* — Jaymi Della

(57) ABSTRACT

A forceps for use in surgery for dissecting tissue includes a pair of jaw members movable from an open position in spaced relation relative to one another to a closed position. The jaw members each have an outer housing extending along the length thereof to a distal end of the jaw members. The outer housing of one of the jaw members includes a textured surface at a distal end configured to interface with and dissect tissue during the movement of the jaw members from the closed to open positions. A dissecting tip may be selectively extendable from a channel defined in one of the jaw members to engage and separate tissue when in the extended position.

3 Claims, 12 Drawing Sheets

(56) References Cited

U.S. PATENT DOCUMENTS

| | | |
|---|---|---|
| 5,810,877 A | 9/1998 | Roth et al. |
| 5,891,142 A | 4/1999 | Eggers et al. |
| 5,893,863 A | 4/1999 | Yoon |
| 5,893,878 A * | 4/1999 | Pierce .......................... 606/207 |
| 5,984,938 A | 11/1999 | Yoon |
| 6,083,223 A | 7/2000 | Baker |
| 6,113,598 A | 9/2000 | Baker |
| 6,270,508 B1 | 8/2001 | Klieman et al. |
| 6,685,724 B1 | 2/2004 | Haluck |
| 6,689,131 B2 | 2/2004 | McClurken |
| 6,702,810 B2 | 3/2004 | McClurken et al. |
| 6,808,525 B2 | 10/2004 | Latterell et al. |
| 6,860,880 B2 | 3/2005 | Treat et al. |
| 7,101,372 B2 | 9/2006 | Dycus et al. |
| 7,131,970 B2 | 11/2006 | Moses et al. |
| 7,267,677 B2 | 9/2007 | Johnson et al. |
| 2001/0021861 A1* | 9/2001 | Boebel et al. ................. 606/207 |
| 2003/0069571 A1 | 4/2003 | Treat et al. |
| 2004/0030330 A1 | 2/2004 | Brassell et al. |
| 2005/0033278 A1 | 2/2005 | McClurken et al. |
| 2005/0255421 A1* | 11/2005 | Michaelson ....................... 433/4 |
| 2006/0116675 A1 | 6/2006 | McClurken et al. |
| 2007/0118115 A1* | 5/2007 | Artale et al. ..................... 606/51 |
| 2007/0270798 A1* | 11/2007 | Lu et al. .......................... 606/51 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| EP | 1683496 | 6/2003 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 92/06642 | 4/1992 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

(56) References Cited

OTHER PUBLICATIONS

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.

(56) References Cited

OTHER PUBLICATIONS

Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

BLUNT TISSUE DISSECTION SURGICAL INSTRUMENT JAW DESIGNS

BACKGROUND

1. Technical Field

The present disclosure relates to forceps for manipulating various types of tissue. More particularly, the present disclosure relates to open, laparoscopic or endoscopic forceps that manipulate various types of tissue.

2. Description of the Related Art

In many surgical procedures, body vessels, e.g., blood vessels, ducts, adhesions, fallopian tubes, etc. are sealed to defunctionalize or close the vessel. Such sealing procedures often require blunt dissection of patient tissue. Working with viable moist and low friction tissue requires the surgeon to use comparatively sharp devices and comparatively high tension to effectively separate the tissue.

SUMMARY

The present disclosure relates to a surgical forceps that enables dissection of tissue with comparatively reduced force, thereby improving tissue division and repeatability of performance. The forceps is for use in surgery for dissecting tissue, and includes a pair of jaw members movable from an open position in spaced relation relative to one another to a closed position. The jaw members each have an outer housing extending along the length thereof to the distal end. One (or both) of the outer housings of the jaw members includes a textured surface at a distal end that is configured to interface with and dissect tissue during the movement of the jaw members from the closed to open positions. The textured surface may include a series of peaks and troughs. A tip defined by one of the series of peaks may include a blunt profile. The textured surface may exhibit at least partially a rounded saw tooth profile. The textured surface may exhibit at least partially a square wave profile or a sine wave profile.

The present disclosure relates also to a forceps for use in surgery for dissecting tissue that includes a pair of jaw members movable from an open position in spaced relation relative to one another to a closed position. The jaw members each have an outer housing extending along the length of the jaw members to the distal end of the jaw members. The outer housing of one or both jaw members defines a channel therein for housing a selectively extendable dissecting tip. The dissecting tip is selectively extendable from the channel to engage and separate tissue when in the extended position during movement of the jaw members from the closed position to open positions. At least one of the jaw members may include the textured surface and features described above.

The present disclosure also relates to a forceps for use in surgery for dissecting tissue that includes a pair of jaw members movable from an open position in spaced relation relative to one another to a closed position. The jaw members each have an outer housing extending along the length of the jaw members to the distal end. The outer housing of one or both jaw members defines a channel therein for housing a selectively extendable dissecting tip. The dissecting tip includes a shaft portion having a curved flange at a distal end thereof that is configured such that movement of the curved flange transversely to the jaw members engages tissue. The curved flange may include an inner periphery having a sharpened edge.

In one embodiment, a dissecting tip may be included that has a shaft portion having a rake member at a distal end thereof. The rake member may include two or more prongs each defining a tip. At least one notch may be defined between two adjacent prongs that is configured to capture tissue therein to facilitate dissection of tissue.

The present disclosure also relates to a method for dissecting tissue that includes the step of providing a forceps for use in surgery for dissecting tissue having a pair of jaw members movable from an open position in spaced relation relative to one another to a closed position. The jaw members each have an outer housing extending along the length of jaw of the jaw members to the distal end thereof. One (or both) of the outer housings of the jaw members includes a textured surface at a distal end thereof. The method also includes the step of positioning the distal ends of the jaw members adjacent tissue when the jaw members are aligned in the closed position; and moving at least one jaw member relative to the other jaw member from the closed to open positions to dissect tissue.

BRIEF DESCRIPTION OF THE DRAWINGS

Various embodiments of the present disclosure are described herein with reference to the drawings wherein.

DETAILED DESCRIPTION

Figure 1:
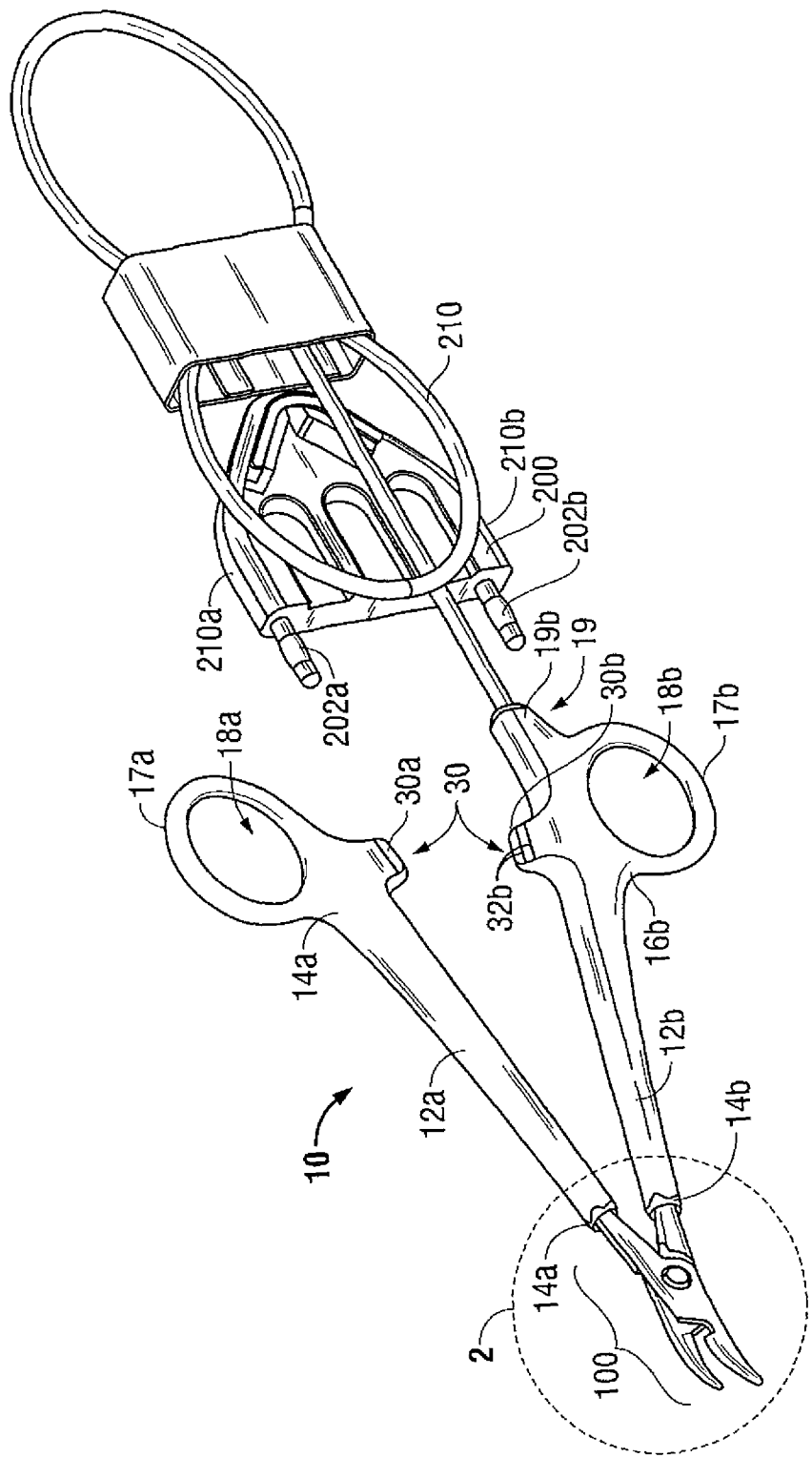
FIG. 1 is a left, perspective view of a forceps according to an embodiment of the present disclosure.

Various embodiments of the present disclosure are described hereinbelow with reference to the accompanying drawings. Well-known functions or constructions are not described in detail to avoid obscuring the present disclosure in unnecessary detail. Those skilled in the art will understand that the present disclosure may be adapted for use with either an endoscopic/laparoscopic instrument or an open instrument; however, different electrical and mechanical connections and considerations apply to each particular type of instrument. The novel aspects with respect to vessel and tissue sealing are generally consistent with respect to both the open and endoscopic/laparoscopic designs. In the drawings and in the description that follows, the term "proximal", as is traditional, will refer to the end of the forceps that is closer to the user, while the term "distal" will refer to the end of the forceps that is further from the user.

Referring now to FIGS. 1-4, a forceps 10 for use with open surgical procedures that can be adapted for tissue dissection according to the present disclosure, as described further below with respect to FIGS. 7-20, includes elongated shaft portions 12a and 12b each having a proximal end 16a and 16b, respectively, and a distal end 14a and 14b, respectively.

The forceps 10 includes an end effector assembly 100 that attaches to distal ends 14a and 14b of shafts 12a and 12b, respectively. As explained in more detail below, the end effector assembly 100 includes pair of opposing jaw members 110 and 120 that are pivotably connected about a pivot pin 150.

Each shaft 12a and 12b includes a handle 17a and 17b disposed at the proximal end 16a and 16b thereof that each define a finger hole 18a and 18b, respectively, therethrough for receiving a finger of the user. Finger holes 18a and 18b facilitate movement of the shafts 12a and 12b relative to one another that, in turn, pivot the jaw members 110 and 120 from an open position (FIG. 2) wherein the jaw members 110 and 120 are disposed in spaced relation relative to one another to a clamping or closed position (FIG. 3) wherein the jaw members 110 and 120 cooperate to grasp tissue 400 (FIG. 4) therebetween.

Figure 4:
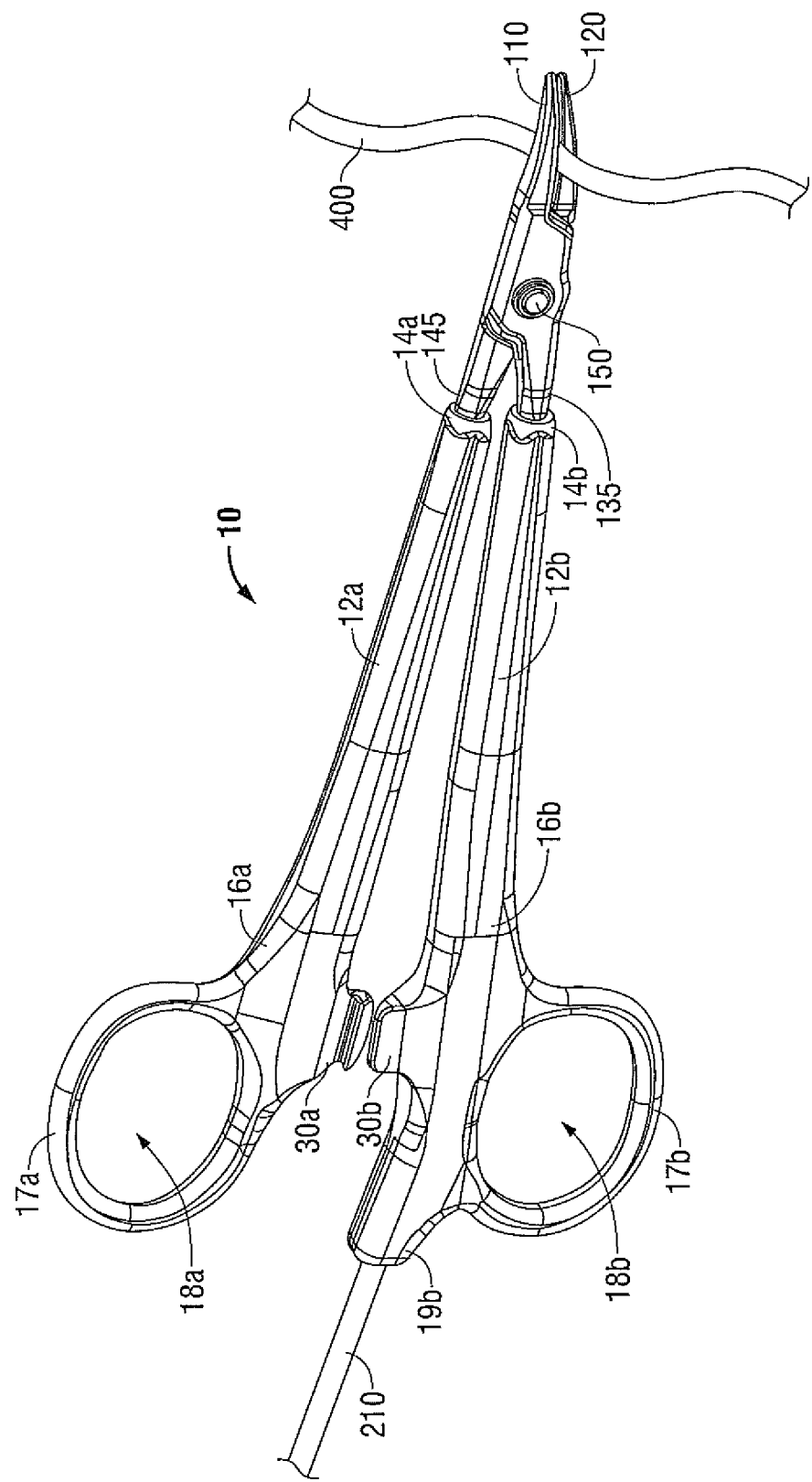
FIG. 4 is a right, perspective view of the forceps of FIG. 1 shown grasping a tissue structure.

A ratchet 30 is included for selectively locking the jaw members 110 and 120 relative to one another at various positions during pivoting. As best shown in FIGS. 1 and 4, a first ratchet interface, e.g., 30a, extends from the proximal end 16a of shaft member 12a towards a second ratchet interface 30b in a generally vertically-aligned manner such that the inner facing surfaces of each ratchet 30a and 30b abut one another upon closure about the tissue 400. Each ratchet interface 30a and 30b includes a plurality of flanges 32a and 32b, respectively, that projects from the inner facing surface of each ratchet interface 30a and 30b such that the ratchet interfaces 30a and 30b interlock in at least one position. As shown in FIGS. 1 and 4, the ratchet interfaces 30a and 30b interlock at several different positions.

Each position associated with the cooperating ratchet interfaces 30a and 30b holds a specific, i.e., constant, strain energy in the shaft members 12a and 12b that, in turn, transmits a specific closing force to the jaw members 110 and 120.

As best illustrated in FIG. 1, one of the shafts, e.g., 12b, includes a proximal shaft connector 19 that is designed to connect the forceps 10 to a source of electrosurgical energy such as an electrosurgical generator (not shown). More particularly, proximal shaft connector 19 is formed by a cover 19a and a flange 19b that extends proximally from shaft 12b. Cover 19a and flange 19b mechanically cooperate to secure an electrosurgical cable 210 to the forceps 10 such that the user may selectively apply electrosurgical energy as needed.

The proximal end of the cable 210 includes a plug 200 having a pair of prongs 202a and 202b that are dimensioned to electrically and mechanically engage the electrosurgical energy generator. The interior of cable 210 houses a pair of leads 210a and 210b that conduct the different electrical potentials from the electrosurgical generator to the jaw members 110 and 120.

Figure 2:
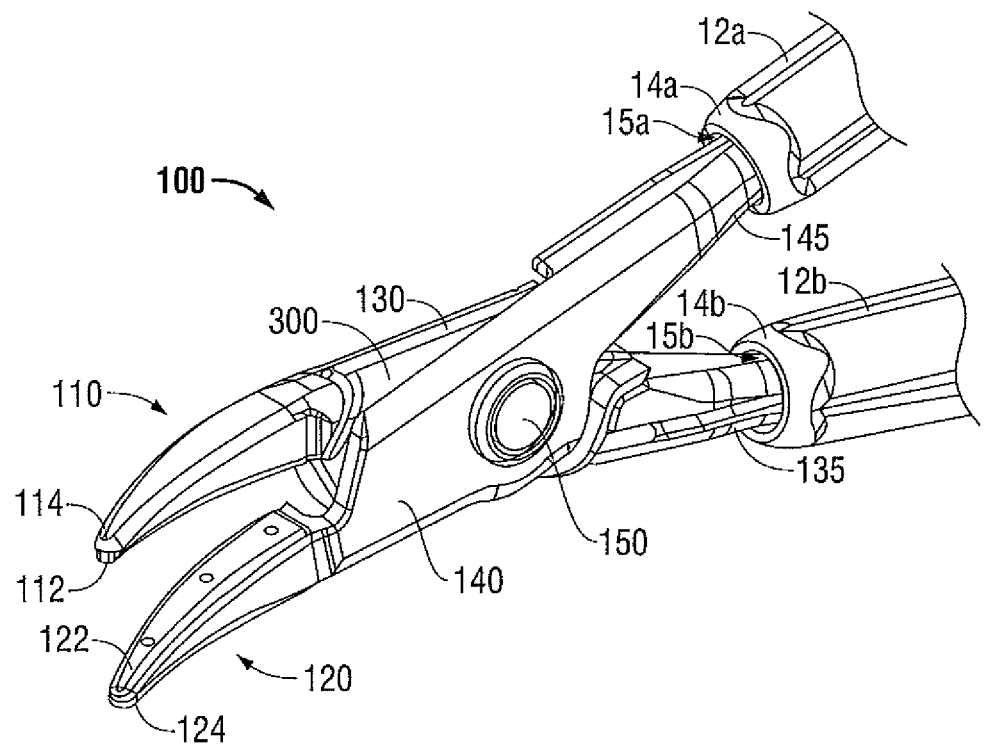
FIG. 2 is an enlarged, perspective view of an end effector assembly of the forceps of FIG. 1 shown in open configuration.
Figure 3:
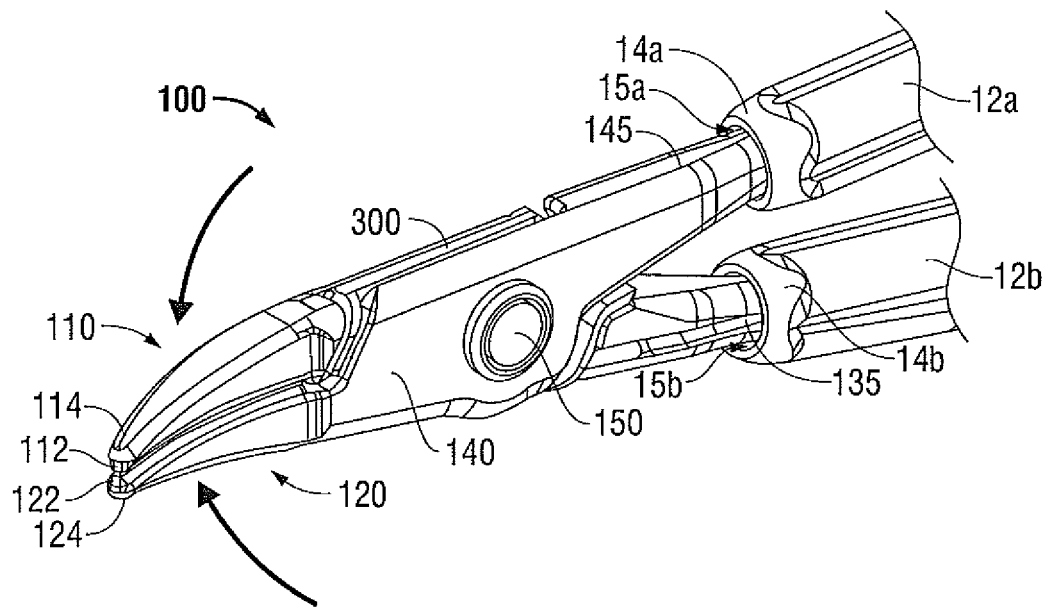
FIG. 3 is an enlarged, perspective view of the end effector assembly of the forceps of FIG. 1 shown in closed configuration.

As best seen in FIGS. 2-3, the two opposing jaw members 110 and 120 of the end effector assembly 100 are pivotable about pin 150 from the open position to the closed position for grasping tissue 400 therebetween. Jaw members 110 and 120 are generally symmetrical and include similar component features that cooperate to permit facile rotation about pivot pin 150 to effect the grasping and sealing of tissue 400. As a result and unless otherwise noted, jaw member 110 and the operative features associated therewith will initially be described herein in detail and the similar component features with respect to jaw member 120 will be briefly summarized thereafter.

Jaw member 110 includes an insulated outer housing 114 that is dimensioned to mechanically engage an electrically conductive sealing surface 112 and a proximally extending flange 130 that is dimensioned to seat a distal connector 300. Outer insulative housing 114 extends along the entire length of jaw member 110 to reduce alternate or stray current paths during sealing and/or incidental burning of tissue 400. The inner facing surface of flange 130 includes an electrically conductive plate (not shown) that conducts electrosurgical energy to the electrically conductive sealing surface 112 upon activation.

Likewise, jaw member 120 include similar elements that include: an outer housing 124 that engages an electrically conductive sealing surface 122; a proximally extending flange 140 that seats the opposite face of the distal connector 300; an electrically conductive plate (not shown) that conducts electrosurgical energy to the electrically conductive sealing surface 122 upon activation.

As previously indicated, forceps 10 can be adapted for tissue dissection according to the present disclosure, as described further below with respect to FIGS. 7-20. Such a forceps is described in U.S. Pat. No. 7,267,677 B2, issued to Johnson et al., entitled "VESSEL SEALING INSTRUMENT."

Figure 5:
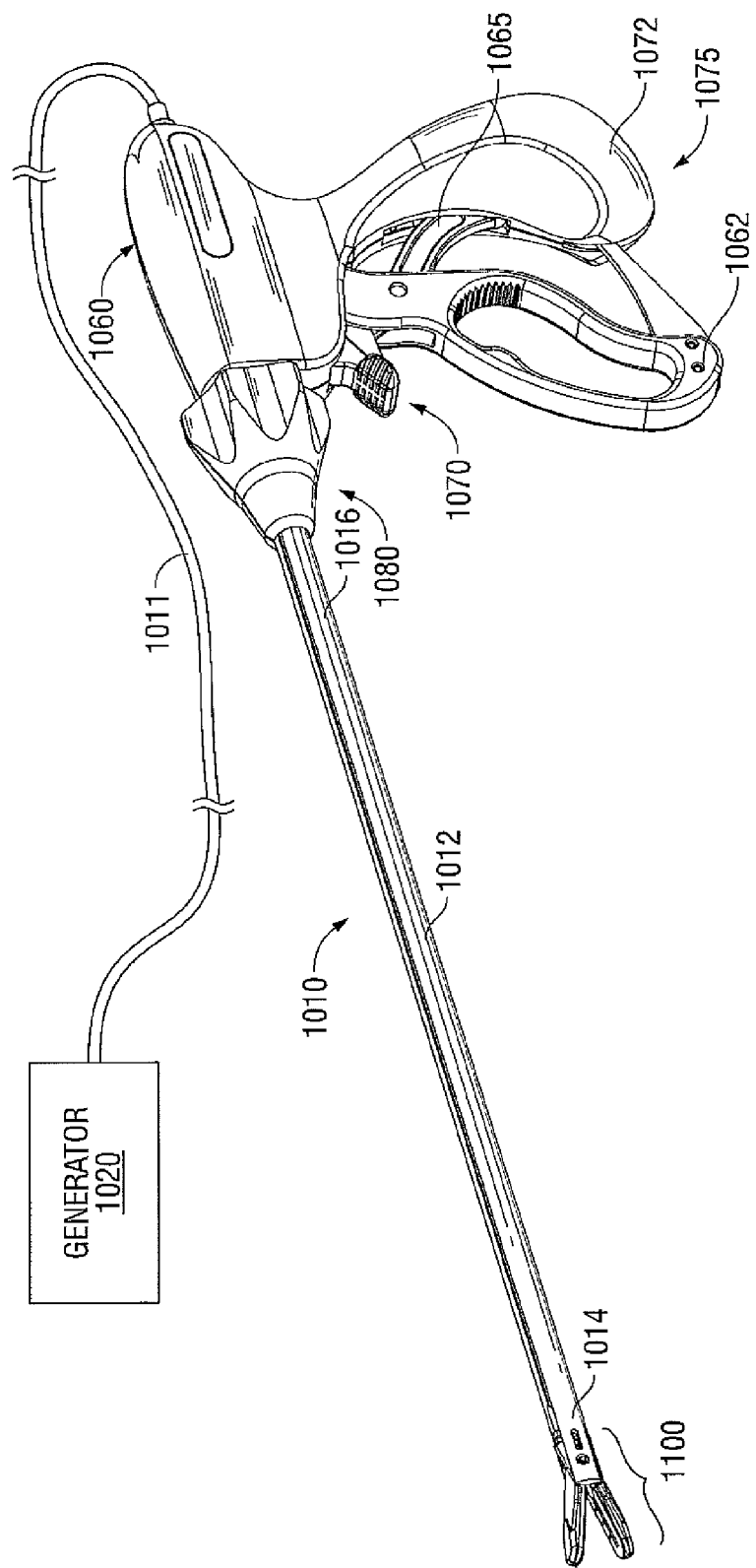
FIG. 5 is a perspective view of a tissue sealing system including a forceps and an energy generator according to one embodiment of the present disclosure.
Figure 6:
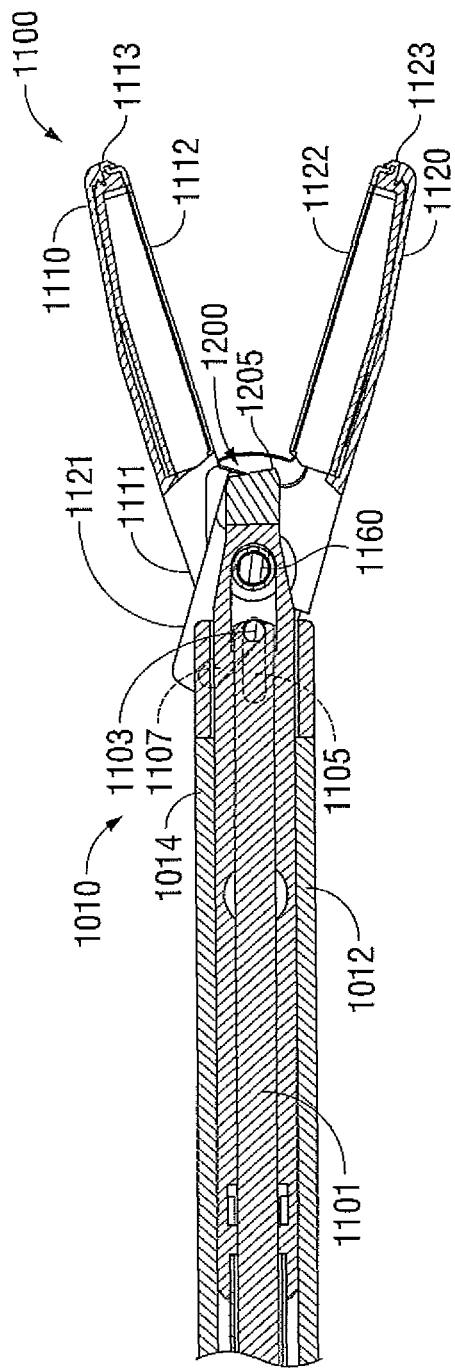
FIG. 6 is a cross-sectional view of a distal end of the forceps of FIG. 1 according to one embodiment of the present disclosure.
Figure 7:
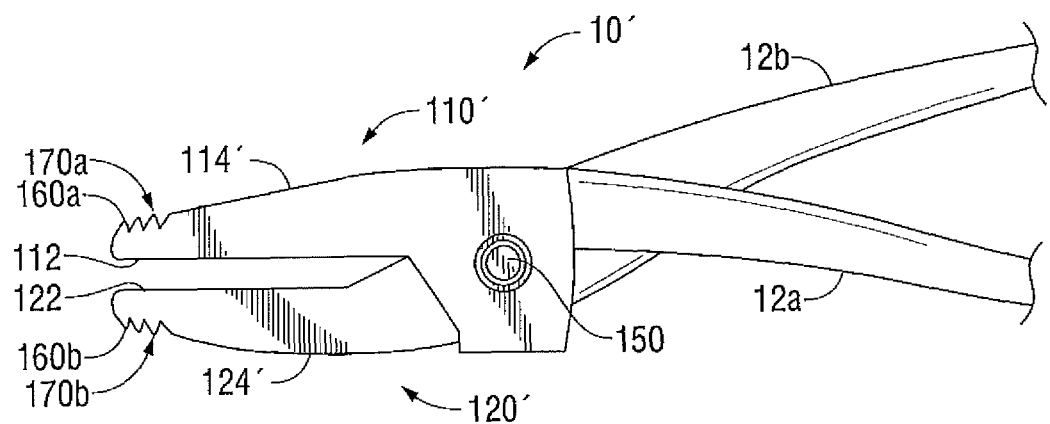
FIG. 7 is a schematically illustrated embodiment of a surgical forceps according to another embodiment of the present disclosure having a textured surface at the respective distal ends of the jaw members to facilitate dissection.

Referring now to FIGS. 5-6, an analogous tissue sealer or forceps 1010 is disclosed that may be adapted for tissue dissection according to the present disclosure.

Forceps 1010 is coupled to the generator 1020 via a cable 1011 that is adapted to transmit energy and control signals therebetween. Forceps 1010 is configured to support an end effector assembly 1100 and includes various conventional features that enable forceps 1010 and end effector assembly 1100 to mutually cooperate to grasp, seal and, if warranted, divide tissue. Forceps 1010 generally includes a housing 1060 and a handle assembly 1075, that includes moveable handle 1062 and handle 1072 that is integral with housing 1060. Handle 1062 is moveable relative to handle 1072 to actuate end effector assembly 1100 to grasp and treat tissue. Forceps 1010 also includes a shaft 1012 that has distal end 1014 that mechanically engages end effector assembly 1100 and proximal end 1016 that mechanically engages housing 1060 proximate a rotating assembly 1080 disposed at the distal end of housing 1060. Rotating assembly 1080 is mechanically associated with shaft 1012. Movement of rotating assembly 1080 imparts similar rotational movement to shaft 1012 that, in turn, rotates end effector assembly 1100.

End effector assembly 1100 includes two jaw members 1110 and 1120 having proximal ends 1111, 1121 and distal ends 1113, 1123, respectively. Jaw members 1110 and 1120 are pivotable about a post 1160 and are movable from a first position wherein jaw members 1110 and 1120 are spaced relative to another, to a second position wherein jaw members 1110 and 1120 are closed and cooperate to grasp tissue therebetween.

Shaft 1012 houses a pushrod 1101 that is operatively coupled to the movable handle 1062 such that when the handle 1062 is moved relative to the handle 1072 the pushrod 1101 moves longitudinally, either proximally or distally within the shaft 1012. The pushrod 1101 includes a push pin 1103 disposed at the distal end 1016 of shaft 1012. Each of the jaw members 1110 and 1120 includes a slot 1105 and 1107, respectively, disposed at the proximal ends thereof. The slots 1105 and 1107 are in mechanical cooperation with the push pin 1103, that is adapted to move within the slots 1105 and 1107. The pin 1103 and slots 1105 and 1107 operate as a cam-follower mechanical linkage. Motion of the pushrod 1101 causes the pin 1103 to slide within respective slots 1105 and 1107 such that the jaw members 1110 and 1120 move either toward or away from each other as the pushrod 1101 is moved longitudinally in a proximal or distal direction, respectively.

Forceps 1010 also includes a trigger assembly 1070 that advances a knife 1200 disposed within the end effector assembly 1100. Once a tissue seal is formed, the user activates the trigger assembly 1070 to separate the tissue along the tissue seal. Knife 1200 preferably includes a sharpened edge 1205 for severing the tissue held between the jaw members 1110 and 1120 at the tissue sealing site. As described and illustrated in more detail below, the jaw members 1110 and 1120 can be adapted with various features according to the present disclosure for blunt dissection of tissue.

Each jaw member 1110 and 1120 includes a sealing surface 1112 and 1122, respectively, disposed on an inner-facing surface thereof. Sealing surfaces 1112 and 1122 cooperate to seal tissue held therebetween upon the application of energy. Sealing surfaces 1112 and 1122 are connected to generator 1020 that communicates energy through the tissue held therebetween.

Turning now to FIGS. 7-12, there is illustrated an instrument for use in surgery for dissecting tissue. More particularly, surgical forceps 10' is an embodiment of the surgical forceps 10 that has been described above with respect to FIGS. 1-4 and that has been adapted to perform either open or endoscopic dissection of tissue. The surgical forceps 10' includes first and second shafts 12a and 12b each having jaw members 110' and 120' extending from a distal end 14a and 14b of the shafts 12a and 12b, respectively. Handles 17a and 17b, corresponding to the respective shafts 12a and 12b, are disposed at proximal ends 16a and 16b, respectively, of the shafts 12a and 12b, for enabling movement of the jaw members 110' and 120' by a user (not shown). As defined herein, the user may be a skilled medical professional such as a surgeon or an automated surgical control system, including a robotic control system that is remotely controlled.

The jaw members 110' and 120' each have an outer insulating housing 114' and 124', respectively, that each extends at least along the length (of jaw) of the jaw members 110' and 120' to distal ends 160a and 160b, respectively. At least one of the outer housings 114' or 124' (or both) includes a textured surface 170a and 170b, respectively, that is configured at the respective distal ends 160a and 160b of the jaw members 110' and 120' to interface with and dissect tissue 400' during the movement of the jaw members 110' and 120'.

Figure 8:
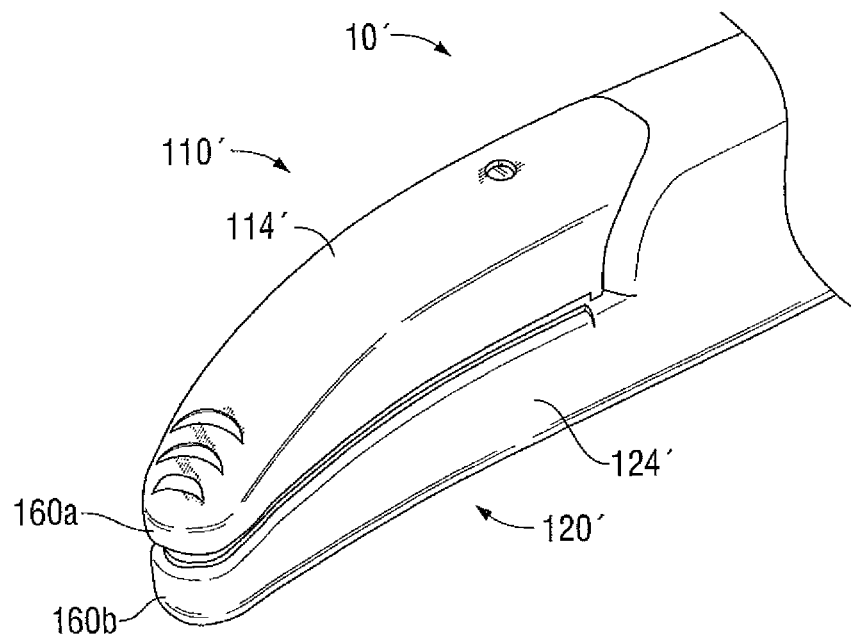
FIG. 8 is a perspective view of the distal ends of the jaw members having etched features to facilitate dissection.
Figure 9:
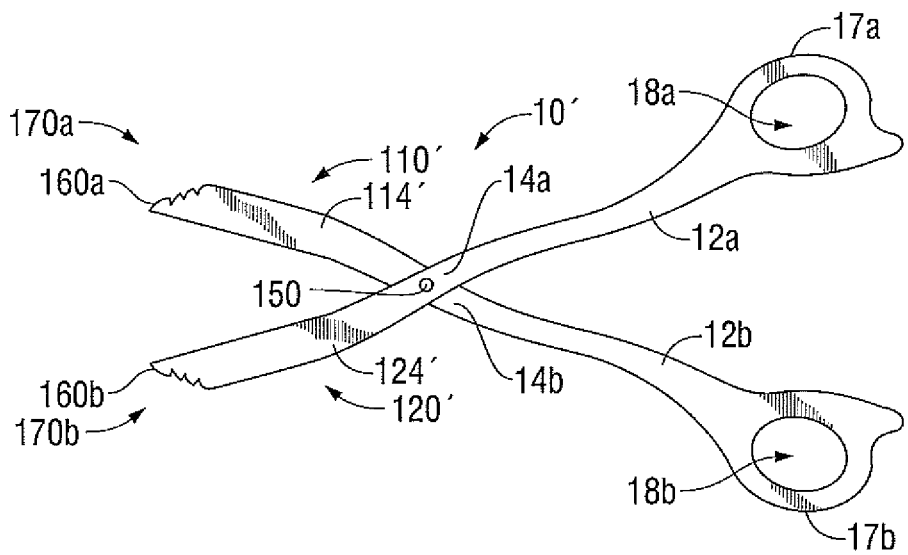
FIG. 9 illustrates the surgical forceps of FIG. 7 in an open configuration.
Figure 10:
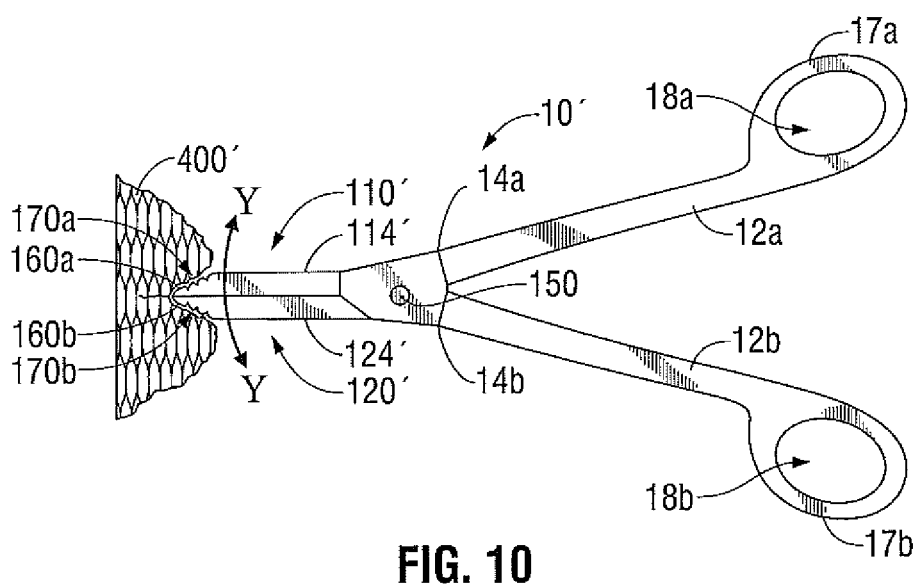
FIG. 10 illustrates the surgical forceps of FIGS. 7 and 9 in a closed configuration wherein the textured surfaces interface with patient tissue prior to opening the forceps to effect tissue dissection.

The first and second shafts 12a and 12b effect movement of the jaw members 110' and 120' relative to one another about a pivot 150 repetitively to and from a position wherein the jaw members 110' and 120' are disposed in spaced relation relative to one another to define an open position as illustrated in FIG. 9 to and from a position wherein the jaw members 110' and 120' cooperate to define a closed position, as illustrated in FIGS. 8 and 10 by at least approaching one another, and/or grasping tissue 400' therebetween, as illustrated by arrow Y-Y.

Figure 11:
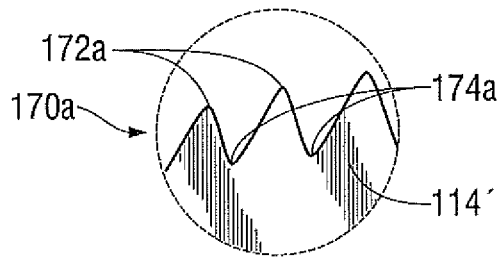
FIG. 11 is a detailed view of the textured surface of the outer insulated housing of the upper jaw member of the surgical forceps of FIGS. 7, 9 and 10.
Figure 12:
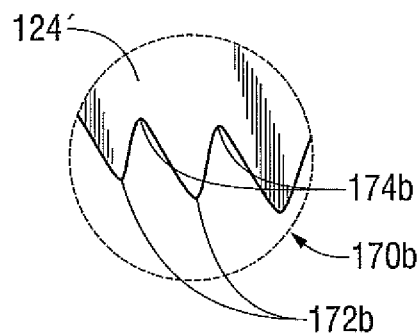
FIG. 12 is a detailed view of the textured surface of the outer insulated housing of the lower jaw member of the surgical forceps of FIGS. 7, 9 and 10.
Figure 11B:
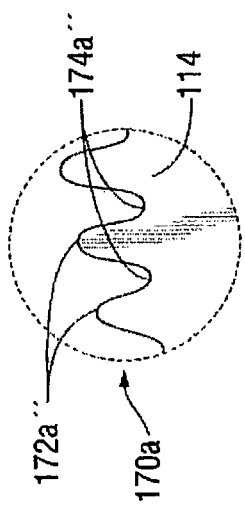
FIG. 11B is a detailed view of the textured surface of the outer insulated housing of the upper jaw member of the surgical forceps of FIGS. 7, 9 and 10 wherein the textured surface exhibits a sine wave profile.
Figure 12B:
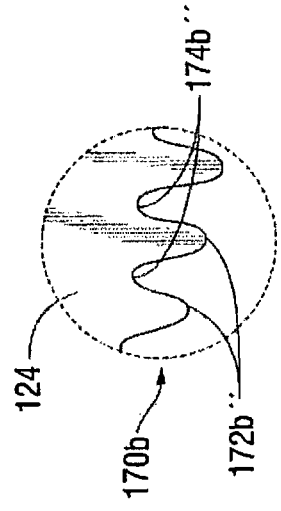
FIG. 12B is a detailed view of the textured surface of the outer insulated housing of the lower jaw member of the surgical forceps of FIGS. 7, 9 and 10 wherein the textured surface exhibits a sine wave profile.
Figure 11A:
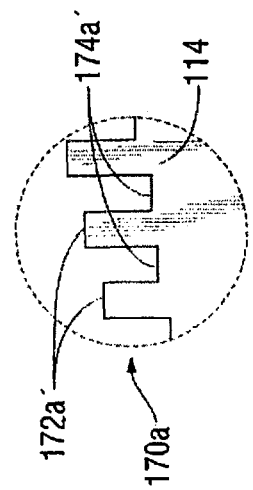
FIG. 11A is a detailed view of the textured surface of the outer insulated housing of the upper jaw member of the surgical forceps of FIGS. 7, 9 and 10 wherein the textured surface exhibits a square wave profile.
Figure 12A:
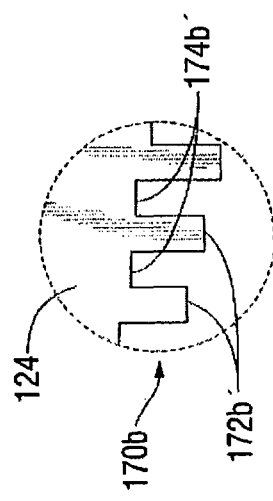
FIG. 12A is a detailed view of the textured surface of the outer insulated housing of the lower jaw member of the surgical forceps of FIGS. 7, 9 and 10 wherein the textured surface exhibits a square wave profile.

As best illustrated in FIGS. 11 and 12, in one embodiment, the textured surfaces 170a and 170b are configured with a peak and trough, e.g., a series of peaks 172a and troughs 174a on jaw member 110' and peaks 172b and troughs 174b on jaw member 120'. The peaks 172a, 172b are configured to facilitate separation of tissue. In one embodiment, the tips defined by the peaks 172a, 172b are configured with a blunt tip to minimize tissue trauma. The peaks 172a, 172b may include varying degrees of sharpness depending upon a particular surgical purpose. For example, the textured surfaces 170a, 170b may exhibit at least partially a rounded saw tooth profile as illustrated in FIGS. 11 and 12. Alternatively, the textured surfaces 170a, 170b may exhibit (at least partially) a square wave profile having peaks 172a', 172b' and troughs 174a', 174b, as illustrated in FIGS. 11A and 12A, respectively, or a sine wave profile having peaks 172a", 172b" and troughs 174a", 174b", as illustrated in FIGS. 11B and 12B, respectively, or other suitable profile (not shown) that facilitates the dissection of tissue according to the embodiments of the present disclosure.

As least one of the insulated outer housings 114' and 124' includes the textured surfaces 170a, 170b configured at the distal ends 160a and 160b of the respective jaw member 110' and 120' to interface with and dissect tissue 400' during the movement of the jaw members 110' and 120', respectively to and from the open position and the closed position.

The textured surfaces 170a and 170b may be over-molded onto the insulating outer housings 114 and 124, respectively, or formed via sandblasting or other suitable methods, such as chemical etching.

Figure 13:
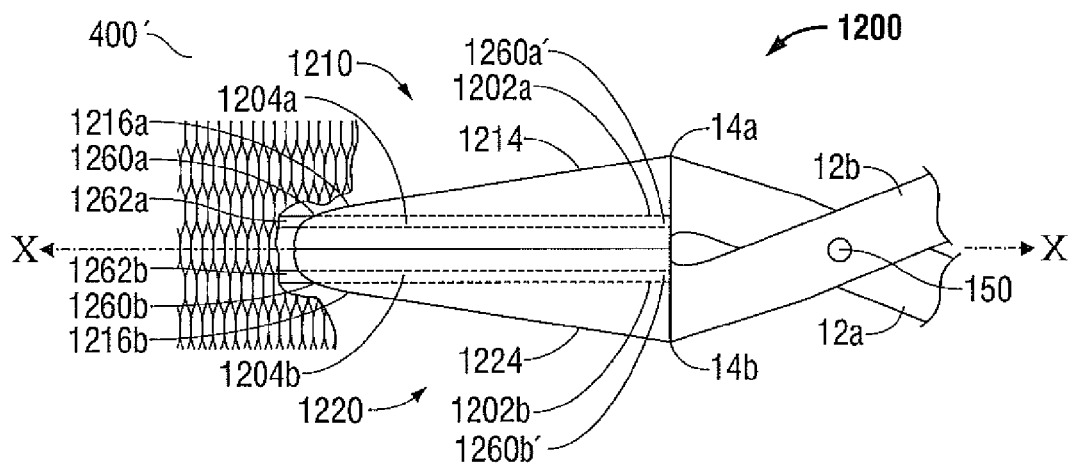
FIG. 13 is a partial view of a surgical forceps in accordance with another embodiment of the present disclosure in a closed configuration.
Figure 14:
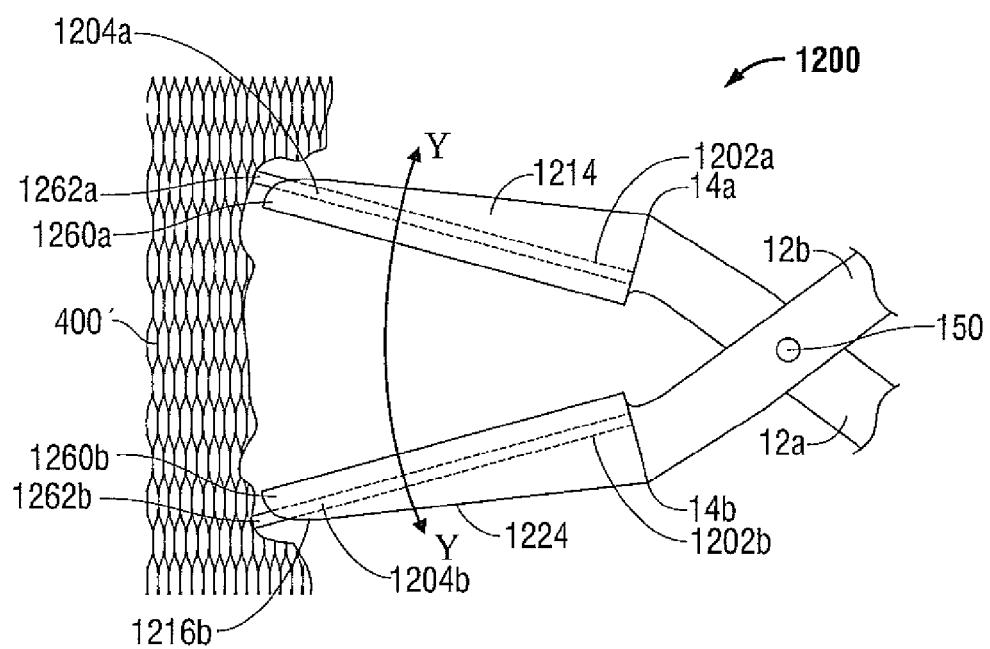
FIG. 14 is a partial view of the surgical forceps of FIG. 13 in an open configuration.

Turning now to FIGS. 13-14, surgical forceps 1200 is an alternate embodiment of the surgical forceps 100 that has been described above with respect to FIGS. 1-4 that also has been adapted to perform dissection of tissue. Forceps 1200 includes first and second shafts 12a and 12b each having jaw members 1210 and 1220 extending from a distal end 14a and 14b of the shafts 12a and 12b, respectively. Handles (see handles 17a and 17b of FIGS. 1 and 4, corresponding to the respective shafts 12a and 12b), are disposed at proximal ends 16a and 16b, respectively, of the shafts 12a and 12b, for enabling movement of the jaw members 1210 and 1220 by a user.

The jaw members 1210 and 1220 each have an outer insulating housing 1214 and 1224, respectively, that extends at least along the length of the jaw members 1210 and 1220 to distal ends 1260a and 1260b, respectively. At least one of the outer housings 1214, 1224, (or both) respectively, each define a channel 1202a and 1202b extending from the respective distal ends 1260a and 1260b along an axial centerline X-X of the jaw member 1210 and 1220. The channels 1202a and 1202b extend at least partially towards respective proximal ends 1260a' and 1260b'.

The forceps 1200 further includes one or more dissecting tips 1204a and 1204b that are configured to reside in the channels 1202a and/or 1202b defined by the outer insulating housings 1214 and 1224, respectively. In the embodiment of FIGS. 13-14, the two dissecting tips 1204a and 1204b as illustrated are adapted to interface with and separate tissue 400' and are selectively extendable from the channels 1202a and 1202b upon actuation of an actuator 40 (see FIG. 20). The dissecting tips 1204a and 1204b, when in the extended position, engage tissue 400' when the jaw members 1210 and 1220 are disposed in a closed position (see FIG. 13) and move in conjunction with the jaw members 1210 and 1220 to separate tissue 400' when the jaw members 1210 and 1220 are moved to an open position (see FIG. 14, and arrow Y-Y).

More particularly, and in a similar manner as with respect to the surgical forceps 10' described above with respect to FIGS. 7-10, the first and second shafts 12a and 12b effect movement of the jaw members 1210 and 1220 relative to one another about pivot 150 repetitively to and from the closed to open positions to dissect the tissue 400' as needed during surgery.

The dissecting tips 1204a and 1204b may be selectively retractable into channels 1202a and 1202b at distal ends 1260a and 1260b of each jaw member 1210 and 1220, respectively. The dissecting tips 1204a and 1204b may be retractable/extendable along the axial centerline X-X of the jaw members 1210 and 1220. The dissecting tips 1204a and 1204b may be formed of thin gauge stainless steel wire and protrude from the channels 1202a and 1202b by a distance ranging to about 0.010 inches (about 0.254 millimeters). For pediatric vascular applications, the gauge of the wire may be about 0.003 inches (about 0.0762 millimeters) and for more aggressive procedures, the gauge of the wire (single strand) may be about 0.02 inches (about 0.508 millimeters). In one embodiment, the dissecting tips 1204a and 1204b include blunt ends at distal ends 1262a and 1262b thereof.

Referring still to FIGS. 13-14, the present disclosure also relates to a method for dissecting tissue that includes the steps: of positioning the forceps 1200, having the dissecting tips 1204a and 1204b that are configured to reside in the channels 1202a and 1202b, respectively, to interface with the tissue 400'; and moving the pair of jaw members 1210 and 1220 to a spaced apart position such that the dissecting tips 1204a and 1204b dissect the tissue 400' during movement thereof. The method may also include the step of extending the dissecting tips 1204a and 1204b of each jaw member 1210 and 1220 to the extended position through the distal ends 1260a and 1260b of the jaw members 1210 or 1220, respectively.

Figure 15:
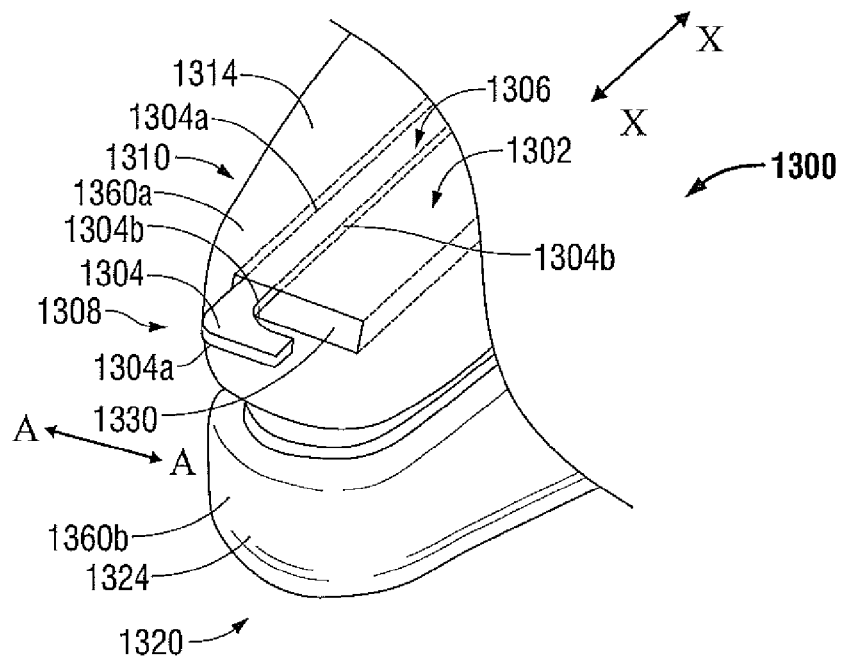
FIG. 15 is a perspective view of the distal ends of jaw members of yet another embodiment of a surgical forceps according to the present disclosure having a curved flange at a distal end of one of the jaw members.
Figure 16:
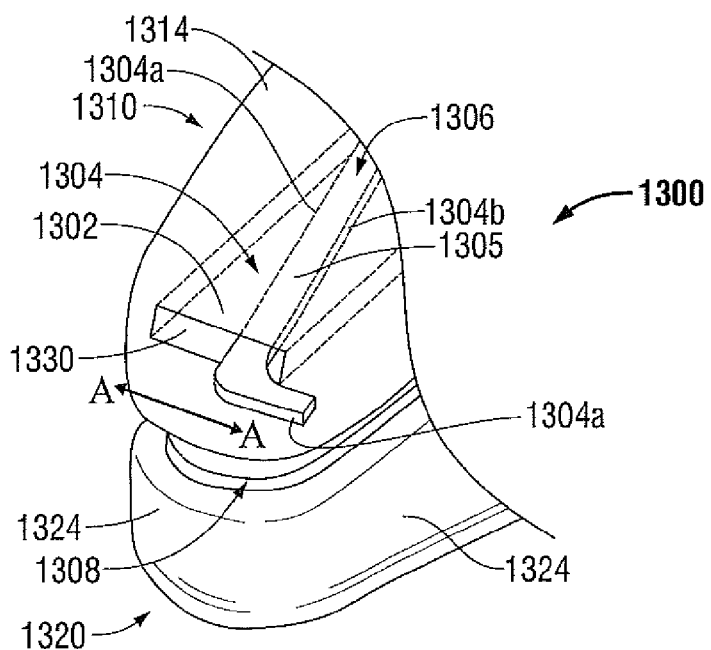
FIG. 16 is a perspective view of the distal ends of the jaw members of FIG. 15 showing the path of movement of the curved cutting flange with respect to the distal end of the jaw member.

FIGS. 15-16 illustrate another embodiment of a forceps 1300 according the present disclosure wherein at least one jaw member 1310 defines a channel 1302 that extends from a distal end 1360a thereof. Again, the channel 1302 extends towards the proximal end (not shown) of the jaw member 1310. Dissecting tip 1304 is configured to reside within channel 1302 and is adapted to interface with and dissect the tissue 400' when extended and actuated (by remote actuator 40, see FIG. 20).

Channel 1302 defines a slot 1330 at a distal end thereof that extends at least partially across the distal end 1360a of the jaw member 1310. Dissecting tip 1304 is selectively extendable from channel 1302 and transversely movable within channel 1302. More particularly, dissecting tip 1304 includes a shaft portion 1305 that includes a curved flange 1304a at a distal end thereof. Upon movement of an actuator, e.g., actuator 40 (see FIG. 20), the shaft portion 1305 and flange 1304a extend from channel 1302 to engage tissue 400' (see FIGS. 13-14). Movement of the same actuator 40 (or a second or a different actuator, not shown) moves the flange 1304a in a transverse direction A-A relative to jaw member 1310 to engage, and in some instances, capture tissue 400'. Flange 1304a may include an inner periphery 1304b that includes a sharpened edge for transecting tissue. Other features may also be employed on the inner periphery 1304b such as blunt edges, teeth, concave or convex edges, etc.

In a similar manner as described above, the blade 1304 may be formed of thin gauge stainless steel wire and protrude from the channel 1302 by a distance ranging to about 0.010 inches (about 0.254 millimeters). Again, for pediatric vascular applications, the gauge of the wire may be about 0.003 inches (about 0.0762 millimeters) and for more aggressive procedures, the gauge of the wire (single strand) may be about 0.02 inches (about 0.508 millimeters).

Referring still to FIGS. 15-16, the present disclosure also relates to a method for dissecting tissue that includes the step of positioning forceps 1300, having the dissecting tip 1304 described above residing within channel 1302, to interface with tissue 400'.

The method also includes the step of dissecting tissue 400' by at least moving the dissecting tip 1304 by extending the curved flange 1304a from the channel 1302 and moving the flange 1304a transversely to engage and, in some instances, capture tissue 400', to facilitate dissection thereof.

Figure 17:
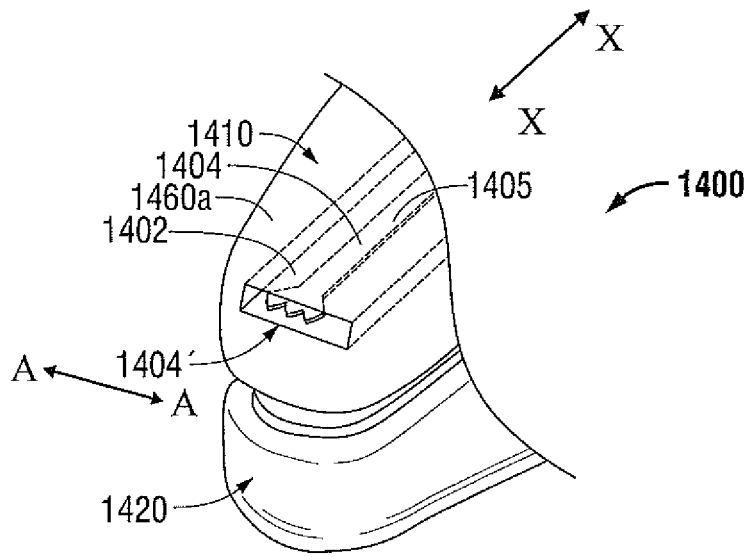
FIG. 17 is a perspective view of the distal ends of jaw members of yet another embodiment a surgical forceps according to the present disclosure having an extendable and movable rake-like dissecting tip.
Figure 18:
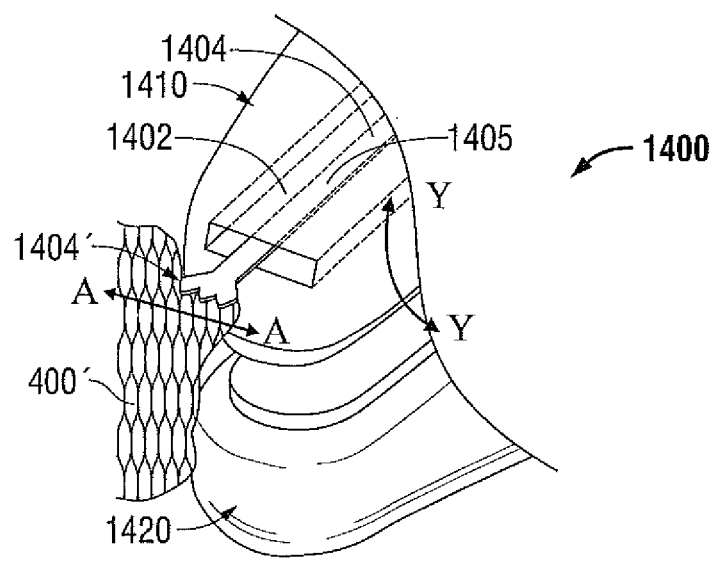
FIG. 18 is a perspective view of the distal ends of jaw members of FIG. 17 showing the path of movement of the rake-like dissecting tip.
Figure 19:
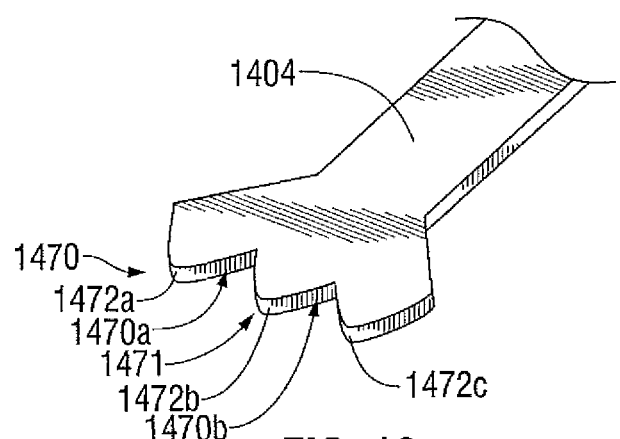
FIG. 19 is an enlarged perspective view of the rake-like dissecting tip.

FIGS. 17-19 illustrate another embodiment of the present disclosure that includes a forceps 1400 having opposing jaw members 1410 and 1420 that are selectively movable in relation to one another from a first open position to a second closed position. One (or both) of the jaw members, e.g., jaw member 1410, includes a channel 1402 defined therein for housing an extendable and movable dissecting tip 1404 having a shaft portion 1405 having a distal end in the form of a rake member 1404' for dissecting tissue. Much like the forceps 1300 and dissecting tip 1304, the dissecting tip 1404 having a distal end in the form of a rake member 1404' is selectively extendable and transversely movable within channel 1402 to dissect tissue 400' (see FIGS. 13-14). The rake member 1404' may include two or more prongs 1472a, 1472b, 1472c associated therewith, each prong defining a tip, that are configured to engage tissue in a rake-like fashion. In addition, the rake member 1404' may include one or more notches 1470a and 1470b that are configured to capture tissue 400 therein to facilitate dissection thereof (see FIGS. 18).

Referring still to FIGS. 17-19, the present disclosure also relates to a method for dissecting tissue that includes the step of positioning forceps 1400, having the dissecting tip having in the form of a rake member 1404' described above residing within channel 1402, to interface with tissue 400'.

The method also includes the step of dissecting tissue 400' by at least moving the rake member 1404' by selectively extending the prongs 1472a, 1472b, 1472c from the channel 1402 and moving the rake member 1404' in a rake-like fashion.

The method may also include the step of moving the rake member 1404' transversely with respect to the distal end 1460a of jaw member 1410, as indicated by arrow A-A in FIG. 18.

The method may also include the step of moving the rake member 1404' in a rake-like fashion such that the one or more notches 1470a and 1470b capture tissue 400', thereby capturing tissue 400' to facilitate dissection thereof.

Figure 20:
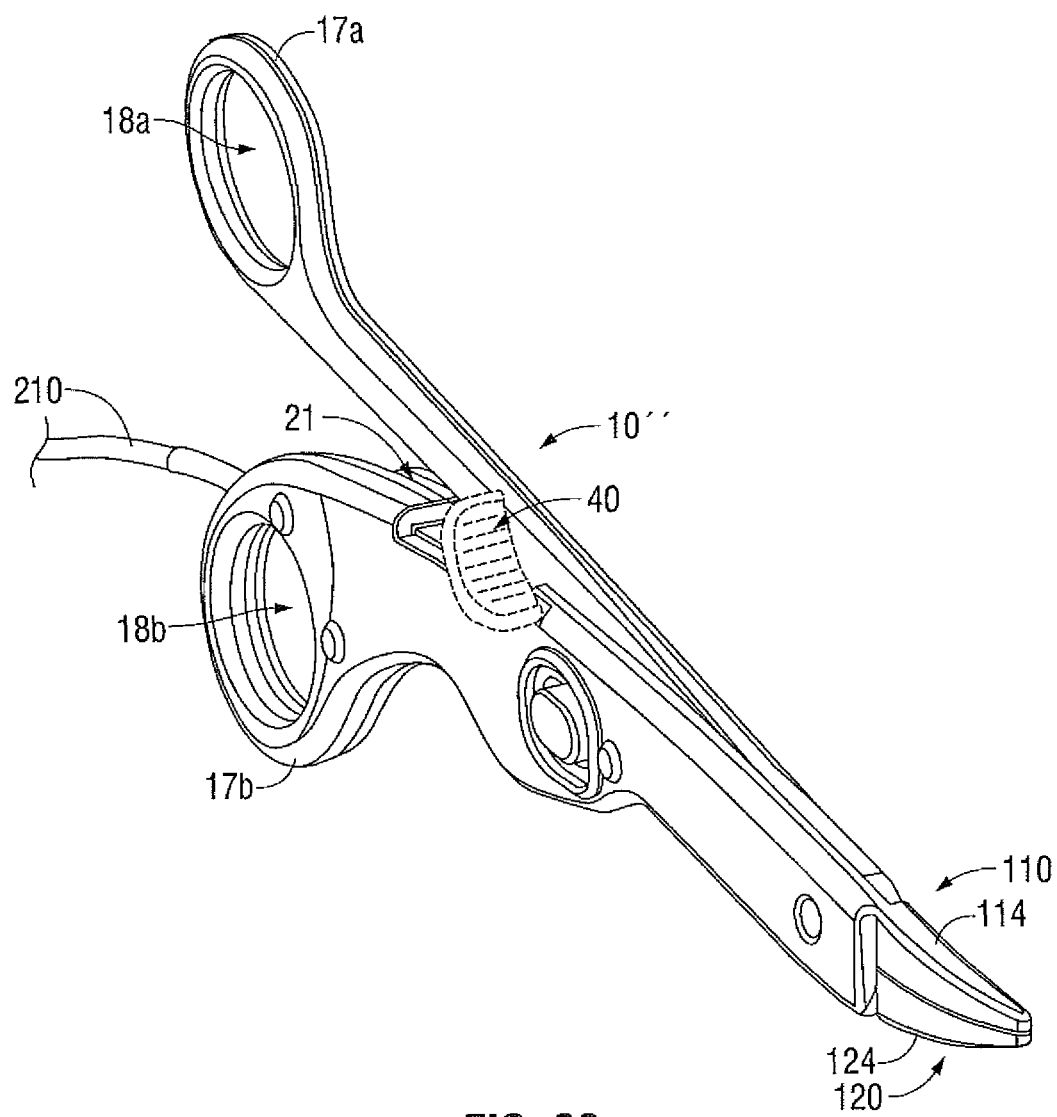
FIG. 20 is a left, perspective view of an open forceps having a blade extension and retraction mechanism according to the present disclosure.

FIG. 20 illustrates a forceps 1500 for use with open surgical procedures that includes an actuating mechanism 40 that may be adapted for use with any of the previously disclosed forceps 1200, 1300, 1400. The actuator 40 may be utilized to retract and/or extend the dissecting tips or rake member as needed during surgery and may be configured to allow the dissecting tips 1204a, 1204b, 1304, 1404 to move transversely to facilitate dissection.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps for use in surgery for dissecting tissue, comprising:
a pair of jaw members movable from an open position in spaced relation relative to one another to a closed position defining a plane of motion of the pair of jaw members, the pair of jaw members each having an outer housing extending along a length of the pair of jaw members to a distal end thereof, and wherein at least one of the outer housings of the pair of jaw members includes a textured surface at the distal end thereof configured to interface with and dissect the tissue during movement of the pair of jaw members from the closed to the open position in the plane of motion defined by the pair of law members such that the textured surface defines a leading edge that is configured to interface with the tissue that is within the plane of motion, the textured surface including a series of peaks and troughs having a complete square wave profile on the leading edge that is configured to interface with the tissue that is within the plane of motion.

2. A forceps according to claim 1, wherein a tip defined by at least one of the series of peaks includes a blunt profile.

3. A forceps for use in surgery for dissecting tissue, comprising:
a pair of jaw members movable from an open position in spaced relation relative to one another to a closed position defining a plane of motion of the pair of jaw members, the pair of jaw members each having an outer housing extending along a length of the jaw members to a distal end thereof, and wherein at least one of the outer housings of the pair of jaw members includes a textured surface at the distal end thereof configured to interface with and dissect the tissue during movement of the pair of jaw members from the closed to the open position in the plane of motion defined by the pair of law members such that the textured surface defines a leading edge that is configured to interface with the tissue that is within the plane of motion, the textured surface including a series of peaks and troughs having a complete sine wave profile on the leading edge that is configured to interface with the tissue that is within the plane of motion.

\* \* \* \* \*